(12) United States Patent
Liu

(10) Patent No.: US 11,020,262 B2
(45) Date of Patent: Jun. 1, 2021

(54) POSTURE, PERFORMANCE, RECOVERY GARMENT DEVICE SYSTEM

(71) Applicant: IFGCure Holdings, LLC, Los Angeles, CA (US)

(72) Inventor: Stephen H. Liu, Los Angeles, CA (US)

(73) Assignee: IFGCURE HOLDINGS, LLC, Los Angeles, CA (US)

( * ) Notice: Subject to any disclaimer, the term of this patent is extended or adjusted under 35 U.S.C. 154(b) by 236 days.

(21) Appl. No.: 16/024,881

(22) Filed: Jul. 1, 2018

(65) Prior Publication Data

US 2019/0254856 A1 Aug. 22, 2019

Related U.S. Application Data

(60) Provisional application No. 62/672,932, filed on May 17, 2018, provisional application No. 62/637,138, filed on Mar. 1, 2018, provisional application No. 62/633,962, filed on Feb. 22, 2018.

(51) Int. Cl.
| | |
|---|---|
| *A61F 5/02* | (2006.01) |
| *A41B 1/08* | (2006.01) |
| *A41D 31/00* | (2019.01) |
| *A41H 43/00* | (2006.01) |

(52) U.S. Cl.
CPC .............. *A61F 5/026* (2013.01); *A41B 1/08* (2013.01); *A41D 31/00* (2013.01); *A41H 43/00* (2013.01); *A41B 2400/22* (2013.01); *A41B 2400/32* (2013.01); *A41D 2300/22* (2013.01)

(58) Field of Classification Search
CPC ..... A61F 5/026; A41D 2300/22; A41F 15/00; A41B 1/18
See application file for complete search history.

(56) References Cited

U.S. PATENT DOCUMENTS

| | | |
|---|---|---|
| 2,575,700 A | 11/1951 | Artzt |
| 2,591,462 A | 4/1952 | Mungo |
| 3,116,735 A * | 1/1964 | Geimer .................. A61F 5/026 450/2 |
| 3,856,004 A | 12/1974 | Cox |
| 4,202,327 A | 5/1980 | Glancy |
| 4,957,103 A | 9/1990 | Young et al. |
| 5,158,531 A | 10/1992 | Zamosky |
| 5,451,200 A | 9/1995 | LaBella et al. |

(Continued)

FOREIGN PATENT DOCUMENTS

| | | |
|---|---|---|
| CN | 2922842 | 7/2007 |
| CN | 201048997 | 4/2008 |

(Continued)

OTHER PUBLICATIONS

International Search Report PCT/US2018/040527 Completed Oct. 12, 2018; dated Oct. 23, 2018 4 pages.

(Continued)

*Primary Examiner* — Tajash D Patel
(74) *Attorney, Agent, or Firm* — Ferguson Case Orr Paterson

(57) ABSTRACT

A garment device and method of manufacture that to support proprioceptive posture rebalance and correction and athletic enhancement and allows and maintains breathability, functionality, range of motion, and aesthetic appeal.

12 Claims, 10 Drawing Sheets

(56) References Cited

U.S. PATENT DOCUMENTS

| | | | |
|---|---|---|---|
| 5,599,286 | A | 2/1997 | Labelle et al. |
| 5,718,670 | A | 2/1998 | Bremer |
| 5,902,261 | A * | 5/1999 | Schwartz ............. A61F 5/3746 128/874 |
| 6,102,879 | A | 8/2000 | Christensen et al. |
| 6,213,922 | B1 | 4/2001 | Afanasenko et al. |
| 6,440,094 | B1 | 8/2002 | Maas |
| 6,676,617 | B1 | 1/2004 | Miller |
| 6,936,021 | B1 | 8/2005 | Smith |
| 7,134,969 | B2 | 11/2006 | Citron et al. |
| 7,153,246 | B2 | 12/2006 | Koscielny et al. |
| 7,395,557 | B1 | 7/2008 | Ledyard |
| 7,662,121 | B2 | 2/2010 | Zours |
| 7,871,388 | B2 | 1/2011 | Brown |
| 8,047,893 | B2 | 11/2011 | Fenske |
| 8,083,693 | B1 | 12/2011 | McKeon et al. |
| 8,308,670 | B2 | 11/2012 | Sandifer et al. |
| 8,516,614 | B2 | 8/2013 | Karasina |
| 8,556,840 | B2 | 10/2013 | Burke et al. |
| 8,795,213 | B2 | 8/2014 | Mills |
| 8,795,215 | B2 | 8/2014 | Rossi |
| 8,887,315 | B2 | 11/2014 | Boynton |
| 8,905,956 | B2 | 12/2014 | Waeger |
| 8,910,317 | B2 | 12/2014 | Decker |
| 8,932,236 | B1 | 1/2015 | McKeon et al. |
| 9,009,863 | B2 | 4/2015 | Decker |
| 9,167,854 | B2 | 10/2015 | Levian |
| 9,168,167 | B2 | 10/2015 | Brown |
| 9,226,534 | B2 | 1/2016 | Puni |
| 9,439,459 | B2 | 9/2016 | Placanica et al. |
| 9,445,932 | B2 | 9/2016 | Boynton |
| 9,456,919 | B2 | 10/2016 | Pollack |
| 9,504,280 | B2 | 11/2016 | Levian |
| 9,883,703 | B2 | 2/2018 | Schultz |
| 9,931,236 | B2 | 4/2018 | Williamson et al. |
| 2004/0107479 | A1 | 6/2004 | Dicker et al. |
| 2005/0197607 | A1 | 9/2005 | Brown |
| 2006/0000478 | A1 | 1/2006 | Taylor |
| 2007/0271671 | A1 | 11/2007 | Okajima |
| 2008/0134409 | A1 | 6/2008 | Karasina |
| 2008/0295230 | A1 | 12/2008 | Wright |
| 2009/0062704 | A1 | 3/2009 | Brown et al. |
| 2010/0050313 | A1 * | 3/2010 | Shackelford, Jr. .......................... A41D 13/1245 2/69 |
| 2010/0192274 | A1 | 8/2010 | Karasina |
| 2011/0131697 | A1 | 6/2011 | Kawahara |
| 2012/0078149 | A1 | 3/2012 | Azimzadeh |
| 2012/0174282 | A1 | 7/2012 | Newton et al. |
| 2013/0047313 | A1 | 2/2013 | Windisch et al. |
| 2013/0053744 | A1 | 2/2013 | Convert et al. |
| 2013/0090521 | A1 | 4/2013 | Lau et al. |
| 2013/0103079 | A1 | 4/2013 | Lau et al. |
| 2013/0104280 | A1 | 5/2013 | Boynton |
| 2013/0296756 | A1 * | 11/2013 | Troncoso ............. A61F 5/026 602/19 |
| 2014/0058307 | A1 | 2/2014 | Marshall |
| 2014/0100501 | A1 | 4/2014 | Burke et al. |
| 2014/0174454 | A1 | 6/2014 | Naef |
| 2014/0221893 | A1 | 8/2014 | Modglin |
| 2014/0242876 | A1 | 8/2014 | Kitagawa |
| 2014/0336556 | A1 | 11/2014 | Pucik |
| 2015/0040286 | A1 | 2/2015 | Schultz et al. |
| 2015/0148727 | A1 | 5/2015 | Collier |
| 2016/0015090 | A1 | 1/2016 | Mazourik et al. |
| 2016/0278963 | A1 | 9/2016 | Webster |
| 2017/0143048 | A1 | 5/2017 | Bucciarelli, III |
| 2017/0160058 | A1 | 6/2017 | Limpisvasti |
| 2017/0216077 | A1 * | 8/2017 | Chahrour ............. A61F 5/028 |
| 2017/0231798 | A1 | 8/2017 | Shin |
| 2018/0153727 | A1 | 6/2018 | Hecht |
| 2018/0317562 | A1 | 11/2018 | Gagliardo |
| 2018/0325714 | A1 | 11/2018 | Froula |

FOREIGN PATENT DOCUMENTS

| | | |
|---|---|---|
| CN | 201048998 | 4/2008 |
| CN | 201048999 | 4/2008 |
| CN | 201049000 | 4/2008 |
| CN | 201049001 | 4/2008 |
| CN | 201049002 | 4/2008 |
| CN | 201160505 | 12/2008 |
| CN | 201316333 | 9/2009 |
| EP | 3315103 | 5/2018 |
| JP | 56-104517 | 8/1981 |
| JP | 62-160924 | 10/1987 |
| JP | 2007119994 | 5/2007 |
| JP | 2008279065 | 11/2008 |
| JP | 2011072323 | 4/2011 |
| JP | 2013112912 | 6/2013 |
| KR | 20140005824 | 11/2014 |
| WO | 9635400 | 11/1996 |

OTHER PUBLICATIONS

Written Opinion of the International Searching Authority dated Oct. 23, 2018 12 pages.

Office Action dated Mar. 17, 2021 for U.S. Appl. No. 16/147,642 (pp. 1-9).

Office Action dated Mar. 17, 2021 for U.S. Appl. No. 16/362,548 (pp. 1-18).

* cited by examiner

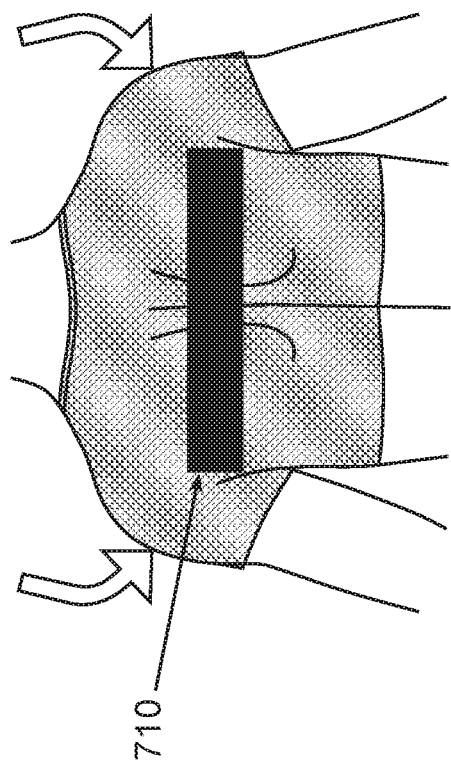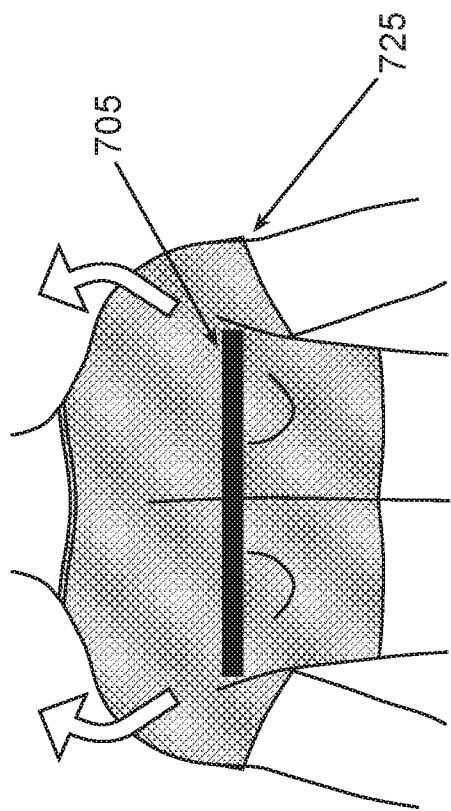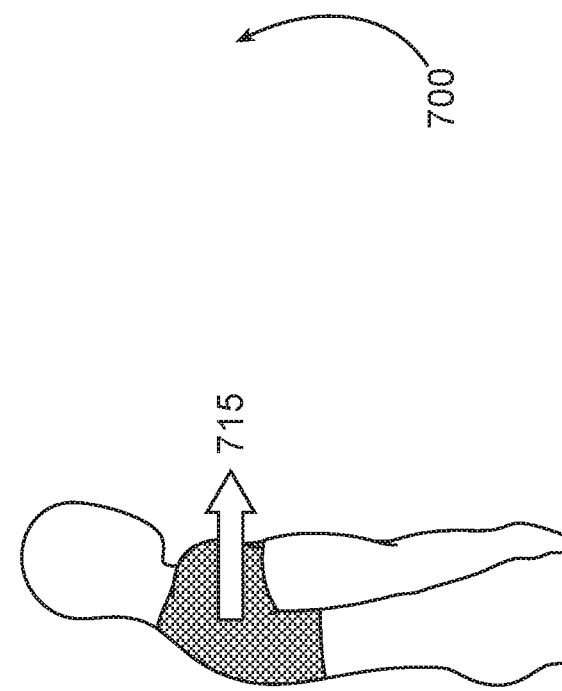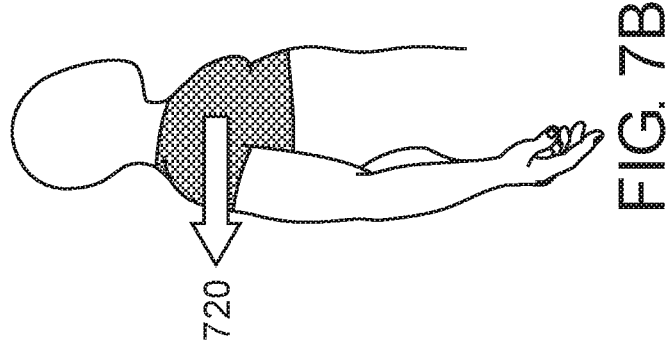
FIG. 7A
FIG. 7B

POSTURE, PERFORMANCE, RECOVERY GARMENT DEVICE SYSTEM

CROSS-REFERENCE TO RELATED APPLICATIONS

This application claims the benefit of U.S. Provisional Application No. 62/672,932 entitled POWER, POSTURE, RECOVERY GARMENT DEVICE SYSTEM, filed May 17, 2018, the disclosure of which are hereby incorporated by reference.

FIELD OF THE INVENTION

The present invention is a garment device and method of manufacture that is configured to be sewn into any shirt-type garment. The present invention is directed to a garment device and method of manufacture in the posture balance, correction and athletic enhancement space. The present invention is directed to a garment device and method of manufacture that supports proprioceptive posture rebalance and correction and athletic enhancement and allows and maintains breathability, functionality, range of motion, and aesthetic appeal.

BACKGROUND OF THE INVENTION

Posture correcting shirts have existed and have been used for several years, the primary goal being to stimulate the body's joints and muscles into better alignment and posture (a slight S-shape of the spine being the gold standard). The importance of having good posture is a well-known and accepted idea among health professionals and non-experts in the field. Good posture helps for both maintaining regular health (back, shoulder, neck pain, etc.) and improving athletic performance, as poor posture during dynamic activities results in inefficient biomechanics and body movement. Indeed, a disruption at any point during the kinetic chain of movement can affect downstream functions as well. Poor posture in the upper body is typically categorized by 'shoulders rolled forward', 'a forward curvature in the thoracic spine', and/or a 'left/right lean of the thoracic spine'. In addition, the inefficient body movement created by poor posture does not allow for full utilization of muscular range of motion and strength and can cause repetitive injury over time.

Typical recovery methods for those suffering from back, neck, and other pain include going to a chiropractor or physical therapy or to seek orthopedic surgeon evaluation. Such medical procedures to correct poor posture involve injections, medications, rehabilitation, and possible surgical correction. As many people cannot afford the time or cost of extensive and costly chiropractor treatments (either short term or long-term treatments), there exists a need in the market for affordable methods and systems to correct and maintain the posture of individuals in attempt to provide:
a) correct functional anatomy;
b) improved muscle efficiency;
c) improved pain relief and minimal pain to users; and
d) creation of good habits so that individuals do not develop poor-posture related pain to begin with.

The first attempts using a wearable garment to refine biomechanical factors that influence posture and kinesthetic states was originated in the 1970's within the Soviet space program, in order to counteract the effects of long-term weightlessness. This device, known as the Adeli suit, is used to treat pediatric patients with postural disabilities due to neurological conditions that lead to brain damage or spinal cord injury. Its design is relatively simple, involving elastic connections between the primary joints, specifically to target positions of antagonistic muscle pairs. However, there are still many other of ways and degrees to which the body can become imbalanced due to disruptions in the kinetic chain of muscle activation.

Muscles devoted substantially to the concepts of balance and posture are sometimes referred to as gravity and anti-gravity muscles; they are the tools that provide upright organisms with the ability to maintain the center-of-gravity (COG) within a stable base of support. Upright balance is attained when a vertical line follows from the center-of-gravity, directly down through this base of support. Any imbalance will cause compensatory abnormalities which will affect alignment within the body's whole musculoskeletal system. Optimized postural alignment is crucial in counteracting the constant downward gravitational forces opposing the body. When the upright force of musculoskeletal architecture and the downward force of gravity are balanced, muscles are able to function with the least amount of work, i.e. peak efficiency.

When the upright body holds better posture, smaller amounts of stress and strain are placed on the muscles, ligaments and bones thereby enhancing their efficiency and increasing bone density and muscle mass in the long term. Opposing the force of gravity, the so called anti-gravity muscles assist to maintain an upright, balanced posture. For the lower body, these muscles consist of namely the soleus muscles, the extensors of the leg, the gluteus maximus, the quadriceps femoris. For the upper body and the muscles of the back, these muscles include the trapezius, the rhomboids, and several smaller groups around the shoulder such as the teres minor and subscapularis. Additionally, the cervico-occipital muscle groups maintain the head in an erect position, thereby preventing it from rolling forward. These muscle groups simultaneously play an important role in the proprioception process, with proprioceptors in the dermal surface sending key information about pressure in the feet to the antigravity muscles through the nervous system. Any weakening of these muscles combined with the continuously working gravitational forces leads to poor postural stability, which affects muscle function. If left untreated, this ultimately leads to degeneration of joints and deformities such as a structural collapse in the foot. Postural alignment is essential to maintain normal length-tension relationships of the muscles especially during dynamic posture, determining the ease with which the body segments align themselves throughout movement. Any disruptions to this alignment throws the kinetic chain of the body off balance, making the person susceptible to a host of injuries. Understanding our limitations at controlling the effect gravitational forces have on the muscles and structure should form the basis of treatment programs.

As one treatment option, posture shirts and girdles were created to fill the burgeoning need of postural correction. Posture shirts and girdles typically contain vertical straps that do not mimic natural anatomical movement. These vertical straps take the wrong approach to correcting a wearer's posture, namely that the straps do not focus on proprioceptive correction to achieve natural postural alignment but instead focus on force. This force creates an unnatural alignment that may push a wearer's shoulders backwards in an outward appearance of better posture but in reality, doesn't achieve much short term or long-term success. Natural posture alignment in the thoracic spine is achieved when posterior muscle groups (i.e. trapezius, rhomboids, latissimus dorsi) and anterior muscle groups (serratus anterior, etc.) are both exerting the same amount of force, thus allowing the body to be balanced. Therefore, garments created in this space targeted this natural (proprioceptive) balancing; however, these garments were not able to fully achieve this goal due to several limitations, including the one listed above.

Further to this idea, the vertical straps that these companies utilize end at the bottom of the buttocks, contributing to the unnatural pull that forces the shoulders back into an improper and unnatural position that does not mimic natural anatomical movement. The corresponding picture would be someone grabbing the bottom of one's shirt from the back and pulling it downwards and tucking it underneath one's glutes; this would certainly force one's shoulders back and posture to be straightened but it would also align the posture in the incorrect form and prove to be extremely uncomfortable. For instance, one shirt of this kind was made from a cotton body with elastic straps that were attached at the front of each shoulder, ran over the back parallel to the spine, and connected at the bottom seam. That same shirt was not only anatomically incorrect, it was also extremely tight (made from a Lycra Spandex material), thus not breathable and uncomfortable. The construction method required also led to these shirts needing to be full-length, which can get hot and sweaty.

Not only does Lycra Spandex material require an extremely tight wear from the user, it's also unsightly and unfashionable and does not translate well to commercial use, since customers are not inclined to wear the garment as their only layer. By wearing an additional layer on top of the Lyrca Spandex to cover the unsightly artificial material layer of the posture correction garment, the breathability issue is compounded with an additional layer of tightness. Due to this combination, individuals typically stop wearing Lyrca Spandex made posture shirts, thus sabotaging the process of building good habits in postural alignment. All of these issues compound to discourage patient wear and compliance since each factor adds an additional negative feature.

One therapeutic method for correcting posture involves the body's proprioceptive sense. An organism uses proprioception to maintain an internal model of its body's orientation in space, a sort of mental avatar representing the mind's best guess as to how its physical limbs are moving. When the primary motor cortex signals the muscles to fire, it also emits an efference signal, also known as a corollary discharge. This second signal has been hypothesized to suppress the subsequent firing of sensory cortex networks when they are inevitably stimulated by the aforementioned motor movement. Therapeutically applied proprioception can be explained by intensifying and subsequently normalizing the afferent proprioceptive mobility-controlling input.

Rather than utilizing vertical straps, one form of the proprioceptive correction technique is the utilization of horizontal straps that contract the rhomboids and the upper trapezius in a horizontal motion that moves the scapula towards the spine and is thus anatomically correct. This natural postural correction is effective because it physically (through the anatomically correct means) corrects a wearer's posture and then passively influences the posture after it is corrected. This is achieved due to the natural tension that the horizontal straps exerts on the wearer, which makes it so that the wearer wants to be in postural correct form without the force of a vertical strap constantly pulling over the shoulder and down to the buttocks region.

Additional systems include U.S. Pat. Nos. 4,202,327, 4,957,103, 4,158,531, 5,451,200, 5,599,286, 5,718,670, 6,102,879, 6,213,922, 6,440,094, 6,676,617, 6,936,021, 7,134,969, 7,153,246, 7,395,557, 7,662,121, 7,871,388, 8,047,893, 8,083,693, 8,308,670, 8,516,614, 8,556,840, 8,795,213, 8,795,215, 8,887,315, 8,905,956, 8,910,317, 8,932,236, 9,009,863, 9,167,854, 9,168,167, 9,226,534, 9,439,459, 9,445,932, 9,456,919, 9,504,280, 9,883,703, 9,931,236, US20040107479, US20050197607, US20060000478A1, US20080134409A1, US20090062704, US20100192274A1, US20120078149, US20120174282, US20130047313, US20130053744, US20130090521, US20130103079, US20140058307, US20140100501, US20140221893 and US20150040286A1.

However, none of the prior art references provide an proprioceptive design that efficiently correctly a wearer's posture. There exists a need for a more comfortable and proprioceptive woven fabric posture re-balance garment that corrects a wearer's posture using anatomically correct movement that allows for shoulder mobility, is breathable and aesthetically pleasing to promote patient compliance, and is not so tight as to be hot and uncomfortable to wear.

Accordingly, the present invention is a device directed to solving all of these problems.

SUMMARY OF THE INVENTION

It is an object of the present invention to provide a more comfortable and proprioceptive woven fabric posture re-balance garment and method of manufacturing thereof.

It is an object of the present invention to provide a more comfortable and proprioceptive woven fabric posture re-balance garment and method of manufacture thereof that corrects a wearer's posture using anatomically correct movement that allows for shoulder mobility, is breathable and aesthetically pleasing to promote patient compliance, is not so tight as to be hot and uncomfortable to wear and can be integrated into any garment.

It is an object of the present invention to provide a garment and method of manufacture thereof that addresses the concern of a lack of patient compliance because it uses horizontal tension rather than vertical tension for correct anatomical posture correction and it can be integrated into any garment, thus allowing for breathability and a greater selection of garments for aesthetic appeal.

Objects of the invention are achieved by providing a garment device for correcting a wearer's posture, the garment device comprising: a mesh body; and a variable tension poly-elastic strap having at least one seam affixed to the strap, wherein the variable tension poly-elastic strap is configured to correct the wearer's posture by naturally pulling the scapula into correct postural alignment.

In certain embodiments, the mesh body is breathable.

In certain embodiments, the mesh body is of variable size(s) and the variable tension poly-elastic strap is of various size(s). In certain embodiments, the variable tension poly-elastic strap is of various thicknesses based upon the size and posture of the wearer.

In certain embodiments, the garment device includes at least two seams and wherein the at least two seams are evenly spaced along the variable tension poly-elastic strap.

In certain embodiments, the garment device includes at least four seams and wherein the at least four seams are evenly spaced along the variable tension poly-elastic strap.

In certain embodiments, the garment device includes more or less than two seams or four seams.

In certain embodiments, the garment device includes a plurality of integration intersections to attach to a secondary garment, such as a shirt.

In certain embodiments, the mesh body in the garment device is made from materials chosen from the group consisting of nylon, spandex, cotton, polyester, chiffon, denim, lace, leather, wool, or a combination thereof.

In certain embodiments, the wearer's posture is corrected physically and proprioceptively with the garment device.

In certain embodiments, the garment device is configured to be conveniently integrated with a secondary garment device via at least one integrated intersection, wherein the at least one integrated intersection is located at a position chosen from a group consisting of: along the nuchal point, along the axilla, around the midsection, or a combination thereof.

In certain embodiments, the integrated intersections are along the collar of a shirt, underneath the armpit of a wearer, along the side of the midsection of the shirt, along the inner seams of a shirt and combinations thereof.

In certain embodiments, the variable tension poly-elastic strap is oriented in a manner chosen from the group consisting of: primarily horizontal, primarily vertical, primarily diagonal, or a combination thereof.

In certain embodiments, the mesh body has a variable length selected from a group consisting of: a shortened length stopping just below the chest, an extended length stopping below the waist, and a medium length stopping at the bellybutton/midsection length.

In certain embodiments, the variable tension poly-elastic strap provides postural support to a wearer suffering from less than ideal posture, or suffering a related malady selected from the following group consisting of: rounded shoulders, scapular dysknesis, kyphosis, forward head, lordosis, scoliosis, rounded shoulder from cervical spine injury, rotator cuff tears, shoulder pathologies, acromioclavicular joint separation, arthritis, and general posterior musculature weakness.

In certain embodiments, the variable tension poly-elastic strap provides postural support to a wearer suffering from rounded shoulders from cervical spine pathology, rotator cuff, shoulder pathology, including but not limited to, AC Joint, Arthritis, AC Separation.

In certain embodiments, the garment device corrects the wearer's posture through a form of direct physical therapy and indirectly through proprioceptive feedback.

In certain embodiments, the garment device includes a casing integrated into the poly-elastic strap. In certain embodiments, the casing envelopes the poly-elastic strap to provide comfort to a wearer. In certain embodiments, the casing is made of the fabric of a secondary garment to which the garment device is connected to or sewn into.

In certain embodiments, the garment device corrects the wearer's posture by pulling the shoulder of the wearer to the posterior, thus placing the scapula in the proper anatomical location.

In certain embodiments, the mesh body includes sleeves, wherein the sleeves of the mesh body extend at least below the deltoid of the wearer. In certain embodiments, the mesh body includes sleeves, wherein the sleeves of the mesh body extend to fit a long sleeve or short sleeve shirt.

In certain embodiments, the garment device is configured to be sewn or attached into any existing item of clothing or is pre-sewn in a production pipeline.

In certain embodiments, the garment device includes anti-microbial materials, moisture wicking materials or a combination thereof.

In certain embodiments, the variable tension poly-elastic strap is designed to relieve all tension in the garment device when the wearer is standing or sitting with correct postural alignment. In certain embodiments, the variable tension poly-elastic strap ceases posterior pull. In certain embodiments, the garment device allows for a full range of motion for the wearer and the restriction of movement is minimized.

In certain embodiments, the garment device is configured to be sewn into a secondary garment and is graded specifically for different ranges in garment device size via corresponding different lengths of the poly-elastic strap. In certain embodiments, the garment device is configured to be attached to a secondary garment via the integrated intersections.

In certain embodiments, the garment device assists the wearer for shoulder muscle rebalance, shoulder rehabilitation, shoulder recovery, shoulder training, scapula rebalance, and/or muscular tension rebalance.

In certain embodiments, the garment device corrects musculo-skeletal realignment, which in turn improves blood circulation in the wearer.

In certain embodiments, the variable tension poly-elastic strap and the breathable mesh of the garment device are configured to improve athletic performance. In certain embodiments, athletic performance is improved because as a wearer's movements become more efficient due to improved posture.

In certain embodiments, the garment device is form-fitting and designed to conform to the wearer's body.

In certain embodiments, the garment device supports the performance, posture and recovery in the wearer.

Other objects of the invention are achieved by providing a method for manufacturing a garment device for correcting a wearer's posture, comprising: providing a mesh body; inserting a variable tension poly-elastic strap with at least one vertical seam into an elastic strap casing that is stitched onto the mesh body, wherein the variable tension poly-elastic strap is configured to correct the wearer's posture by naturally pulling portions of the musculo-skeletal frame into correct postural alignment.

In certain embodiments, the variable tension poly-elastic strap includes two or more vertical seams. In certain embodiments, for devices for women, the variable tension poly-elastic strap includes two seams. In certain embodiments, for devices for men, the variable tension poly-elastic strap includes four seams. In certain embodiments, more or less seams are provided. In certain embodiments, the seams are evenly spaced.

In certain embodiments, the mesh body is replaced by a similar material providing sufficient tension or rigidity.

In certain embodiments, the variable tension poly-elastic strap is integrated into the mesh body to allow for a wearer's forward range of motion.

In certain embodiments, the length of the variable tension poly-elastic strap is graded specifically to each garment size. In certain embodiments, the elastic strap is configured around the medial point of the scapula of the wearer.

In certain embodiments, a casing is integrated into the construction of the elastic strap to provide comfort to the wearer.

In certain embodiments, the type of stitching method is chosen from a group consisting of: blind, double blind, flatlock, overlock, welded, active, or a combination thereof.

Other objects of the invention are achieved by providing a method for simultaneously passively and actively influencing a wearer's posture through biasing muscle forces, comprising: providing a mesh body providing sufficient tension or rigidity, the mesh body made from materials chosen from a group consisting of: nylon, spandex, polyester, or a combination thereof; providing an elastic strap integrated into the mesh body, wherein the elastic strap creates a variable tension force between at least one focal points in a wearer.

Other objects of the invention are achieved by providing a garment device for correcting a user's posture, the garment device comprising: a mesh garment made from nylon and spandex; and a variable tension poly elastic strap with four evenly spaced, vertical seams to target and disperse tension in a wearer.

In certain embodiments, the mesh garment has a shortened length, stopping just below the chest.

In certain embodiments, the variable tension poly elastic strap provides support to the wearer. In certain embodiments, the variable tension poly elastic strap provides support to the wearer's posture by naturally pulling the scapula into correct postural alignment.

In certain embodiments, the variable tension poly elastic strap is incrementally adjusted to improve the wearer's posture in set intervals.

In certain embodiments, the correction of a wearer's posture is corrected proprioceptively. In certain embodiments, the device corrects the wearer's posture by pulling the shoulder of the wearer to the anterior, thus placing the scapula in the proper anatomical location.

In certain embodiments, the device improves athletic performance. In certain embodiments, the device contains anti-microbial moisture wicking and is protects against ultra-violet (UV) rays.

In certain embodiments, the tension straps are designed to relieve all tension in the garment when the wearer is standing with correct postural alignment and cease the posterior pull. In certain embodiments, the device allows a full range of motion for the wearer. In certain embodiments, the device can be sewn into any garment and is graded specifically for each garment size via a poly-elastic strap.

In certain embodiments, the device allows for ease of breathing and a more comfortable fit. In certain embodiments, the device assists the wearer in muscular tension rebalance.

In certain embodiments, the device assists the wearer for shoulder muscle rebalance, shoulder rehabilitation, shoulder recovery, and/or shoulder training. In certain embodiments, the device assists the wearer with scapula rebalance. In certain embodiments, the sleeves of the device do not extend below the biceps of the wearer.

In certain embodiments, the device improves the efficiency of a wearer's posture which increases blood circulation in the wearer and promotes health and general well-being.

Other objects of the invention are achieved by providing a method for creating a garment device for correcting a user's posture, comprising: providing a mesh garment made from nylon and spandex; inserting a variable tension poly elastic strap with four evenly spaced, vertical seams into the mesh garment, wherein the variable tension poly elastic strap targets and disperses tension in a wearer.

In certain embodiments, the elastic strap is graded specifically to each garment size. In certain embodiments, the elastic strap is configured around the medial points of the scapulae.

In certain embodiments, the mesh body garment has an under-layer or an inwardly facing surface designed to resist slippage when donned. The mesh body is required to encase the wearer's upper body and therefore can benefit from an inner surface that adds small, diffusing force by wrapping around the chest and shoulders, which distributes force evenly across the shoulder capsule.

Other objects of the invention are achieved by providing a garment device constructed with a strong power mesh made from 72% nylon and 28% spandex in its current embodiment and designed with a short and loose construction that stops just below the pectoralis major and T-8 vertebrae. Despite the mesh, the garment device does not restrict movement of the shoulder, as the other tight-fitting posture garments in this space do.

Other objects of the invention are achieved by providing a garment device constructed with a strong power mesh made from approximately 70% nylon and approximately 30% spandex in its current embodiment and designed with a short and loose construction that stops just below the pectoralis major and T-8 vertebrae. Despite the mesh, the garment device does not restrict movement of the shoulder, as the other tight-fitting posture garments in this space do.

Other objects of the invention and its particular features and advantages will become more apparent from consideration of the following drawings and accompanying detailed description. It should be understood that the detailed description and specific examples, while indicating the preferred embodiment of the invention, are intended for purposes of illustration only and are not intended to limit the scope of the invention.

BRIEF DESCRIPTION OF THE DRAWINGS

FIG. 7A-7B shows the garment device pulling the shoulders or a wearer.

DETAILED DESCRIPTION OF THE INVENTION

Figure 1:
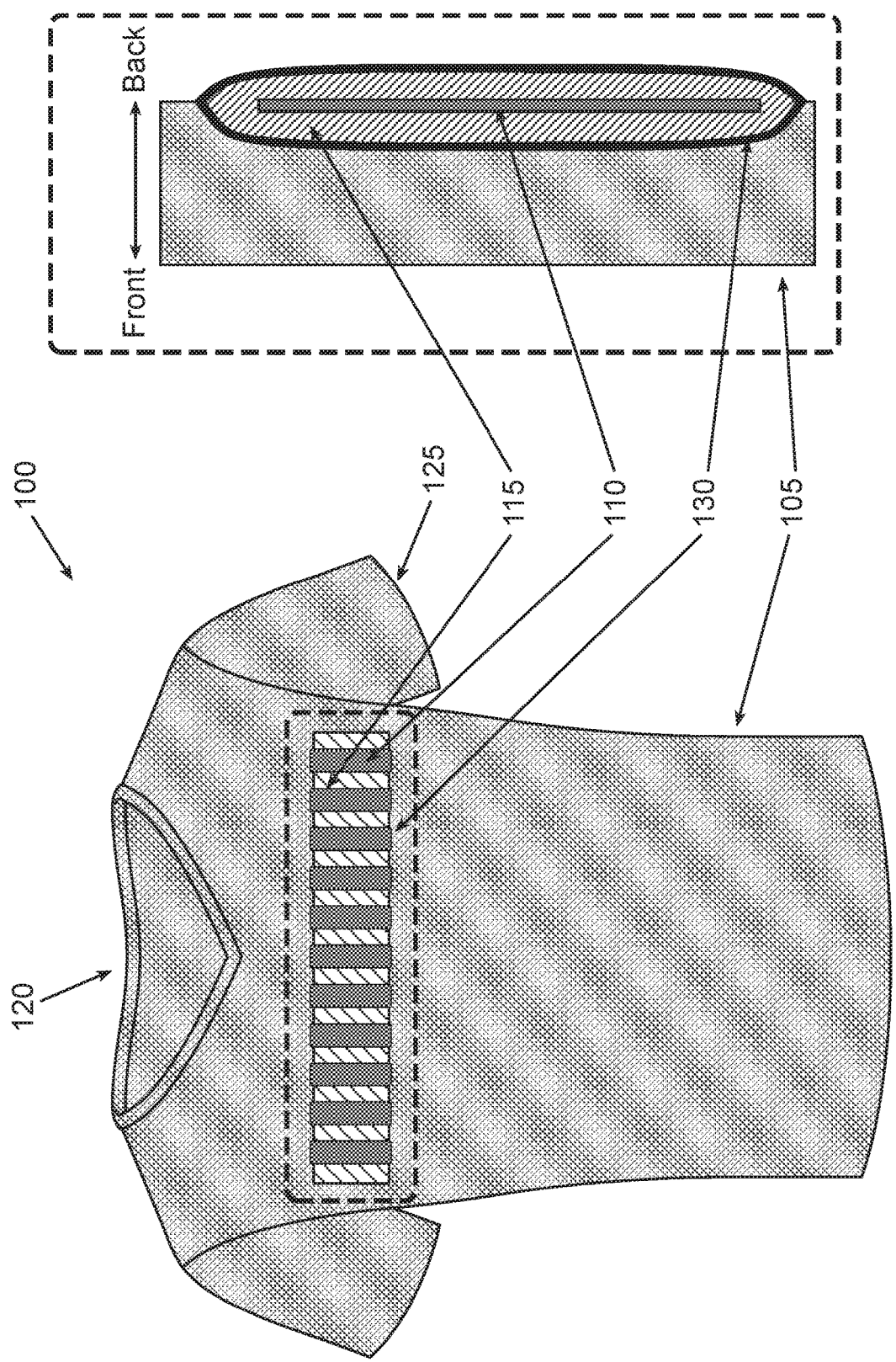
FIG. 1A-1B is an anterior view of the garment device and a zoomed in side-ways view of the elastic strap inside the casing.

The present invention is directed to a garment device that accounts for the limitations of the currently available garments made with Lyrca Spandex and other constricting materials. Branded as the Posture, Performance, Recovery System (PPR)—this is a device that accounts for all three namesake items in its title: (1) proprioceptively correcting a wearer's posture; (2) giving wearers better performance with more motion generated power via better posture and form; and (3) allowing for better recovery via correction of poor posture habits. The garment improves upon previous posture garments through its flexible nature, namely the ability to act as a garment addendum device, i.e. it can be conveniently sewn into any existing garment or come pre-packaged and integrated into another manufactured garment fresh off the production line. Not only does this single handedly solve the problem of unaesthetically pleasing posture garments plaguing the space since its inception (as the garment device is nearly unnoticeable and can accommodate any common garment), it does so while also solving the issues of shoulder restriction and non-breathability through allowing a full range of motion.

The garment device is unisex and not limited by a sizing factor, therefore it is also flexible in the way it corrects a wearer's posture. In other words, the garment device is custom fitted for each wearer by being sewn into the inside of the chosen garment, at various integrated intersections such as near the neck opening area or armpits. For correcting rounded shoulders, an elastic strap is sewn horizontally across the areas of the garment that correspond to connecting the medial points of each scapula, also known as the "shoulder blade". Thus, patients or casual wearers are no longer tasked with finding the specific matching size and overly complex posture correcting garments; they can simply sew any garment device into their own chosen garment.

Aside from its flexible nature of fabrication in accommodating any garment for usage, the garment device achieves its main function of posture correction through a proprioceptive manner that involves creating a substantially parallel amount of tension in the body's anatomical musculature. The garment device mirrors and augments the muscle groups of the Latissimus dorsii, Rhomboids, Trapezius, Posterior Deltoids, Teres Minor, Subscapularis, and Teres Major, among others to create a pull that naturally assists the wearer into scapula adduction (also known as retraction) for correct postural alignment. Once the wearer is in correct postural alignment, the garment device automatically relieves all tension in the garment and ceases the posterior pull that gives the wearer correct posture in the first place. Thus, the wearer will barely notice the device once the wearer has achieved the muscle memory of correct posture.

To understand how the garment device augments the sensory feedback portion of the Rhomboid and Upper Trapezius muscles of the back are the primary muscle groups responsible for the retraction of the shoulder blades. Those muscle groups contract and draw the scapula towards the spine thus drawing the whole shoulder toward the posterior. Most people with less than desirable posture do not adequately contract the aforementioned muscle groups to maintain neutral anatomy and proper posture.

The variable elastic strip of the garment device mimics the anatomical motion of rhomboid and upper trapezius. This is what applies the intense afferent signal to the proprioceptive system, thereby training the system. It is accomplished by the elastic strap cycling between a relief of tension and exertion of tension on the parallel muscle system.

Additional advantages of the garment device include:

"Improves Performance"—It is contemplated that the garment, by retracting the scapula, will assist in weight lifting training regimens and competition, by improving the wearer's form throughout the lift. A retracted scapula creates a more stable base and results in the recruitment of relatively more chest muscle groups, as opposed to the weaker shoulder muscle groups. Due to the user recruiting a stronger muscle as the primary mover for an exercise, there will be faster progress in training and improved performance for competitions.

"Seesaw effect"—As one treatment option, posture shirts were created to fill the burgeoning need of proprioceptive therapy. Posture shirts typically contain elastic straps and special stitching that helps maintain an upright body with correct alignment both skeletal and muscle-wise through the contraction of certain muscles. Natural posture alignment in the thoracic spine is achieved when posterior muscle groups (i.e. trapezius, rhomboids, latissimus dorsi) and anterior muscle groups (serratus anterior, etc.) are both exerting the same amount of force, thus allowing the body to be balanced.

Aside from its flexible nature in accommodating any garment for usage, the garment device achieves its main function of posture correction through a proprioceptive manner that involves creating a parallel amount of tension in the body's anatomical musculature. The garment device mirrors and augments the muscle groups of the Latissimus dorsii, Rhomboids, Trapezius, Posterior Deltoids, Teres Minor, Subscapularis, and Teres Major, among others to create a pull that naturally assists the wearer into scapula adduction (also known as retraction) for correct postural alignment. Once the patient is in correct postural alignment, the garment device automatically relieves all tension in the garment and ceases the posterior pull that gives the wearer correct posture in the first place. Thus, the wearer will barely notice the device once the wearer has achieved the muscle memory of correct posture.

"Attachment point" or integrated intersection—The main attachment point (integrated intersection) is chosen along the posterior rim of the collar, because this point of contact between the two garments is the most stable and least likely to experience shifting. The anatomical position of the attachment point is the nape of the neck, otherwise referred to as the "nuchal" point in medical terminology. In other embodiments, the attachment points include the areas circumscribing the axilla and anterior pectoris.

Posture and Proprioceptive Therapy—the garment devise provides improved results for musculature around the shoulder. The shoulder, or glenohumeral joint, provides the arm with a large range of motion, yet this joint possesses very little intrinsic stability, resembling a ball on a plate more than a ball in a socket. Most stability in the shoulder is provided by the ligaments and muscles surrounding the joint. Proper muscle activation is required to maintain positioning of the humeral head in the glenoid fossa. Adjustments are continuously made to glenohumeral joint position based on feedback information from proprioceptive receptors in the muscles, tendons, ligaments, and receptors in the skin. Proprioception is a complex entity with many interacting components. The brain uses efference copy to initiate and verify active motions. Such verification requires information about musculoskeletal motion sent back to the brain by a variety of sensory receptors in the muscles and skin. The current belief is that muscle spindles, movement encoders in parallel with the muscle, are the predominant proprioceptors with important contributions from cutaneous receptors. Muscle spindle intrafusal fibers in the shortening muscle contract during active motion, possibly to maintain muscle spindle sensitivity.

Rhomboid and Upper Trapezius muscles therapy—The Rhomboid and Upper Trapezius muscles of the back are the primary muscle groups responsible for the retraction of the shoulder blades. Those muscle groups contract and draw the scapula towards the spine thus drawing the whole shoulder toward the posterior. Most people with less than desirable posture do not adequately contract the aforementioned muscle groups to maintain neutral anatomy and proper posture. The garment device consists of two primary types of fabrics that mimic the motion and contraction of the rhomboids and upper trapezius.

The vertically segmented elastic strap, is mounted in the center, posterior of the garment device. The vertically segmented elastic strap, precisely overlays the rhomboids and upper trapezius. When the shirt is donned by the user, the elastic strap is slightly stretched (or extended). Due to the stretch of the elastic, pull is created toward the spine, mirroring the contraction of the rhomboids and upper trapezius. If the user holds perfect posture with his/her own musculature the vertically segmented elastic strap applies very little pressure. As the user allows his/her shoulders to "roll" forward, the vertically segmented elastic strap applies greater tension.

The garment device mesh body (or similar fabric) encapsulates the upper arm, shoulder and upper back. This allows the Vertically segmented elastic strap to attach to the medial point of the scapula. The tension and force of the strap is distributed across the entire front and rear shoulder area diffusing uncomfortable pressure points and providing retraction by "pulling" from the front and rear of the shoulder simultaneously.

This method of retraction differs from other products. Competitors use vertical straps sewn into a garment that run from the upper shoulder or chest, down the back and terminating at the buttox. The force of these straps are applied to the upper insertion points of the straps (which they call NeuroBands). The problem with these types of shirts is that the entire body has to be tight and if the wearer does not exactly fit the garment it is ineffective. The garment device's benefit is that it applies diffused horizontal tension that mirrors the anatomy and the body of the garment can be loose or tight depending upon the user's preference.

Referring now to FIG. 1, this is an anterior view of the garment device 100. It is made out of a strong power mesh 105, which can be composed of a variety of different fabrics and has moderately heavy compression qualities, creating an 'inner structure' that is sewn into a garment via one or more attachment points 120. The garment acts as an inner structure in that it is nearly unnoticeable inside both short and long sleeve garments. In its current embodiment, the garment device has arm seams 125 that stop just below the deltoid and at the mid-bicep level. The anterior and posterior shoulder of the garment is tight fitting and provides moderate compression to the wearer. Although the current embodiment of the garment device is constructed in this fashion, the garment device can be adopted to fit a long sleeve or a longer short sleeve version.

Figure 10:
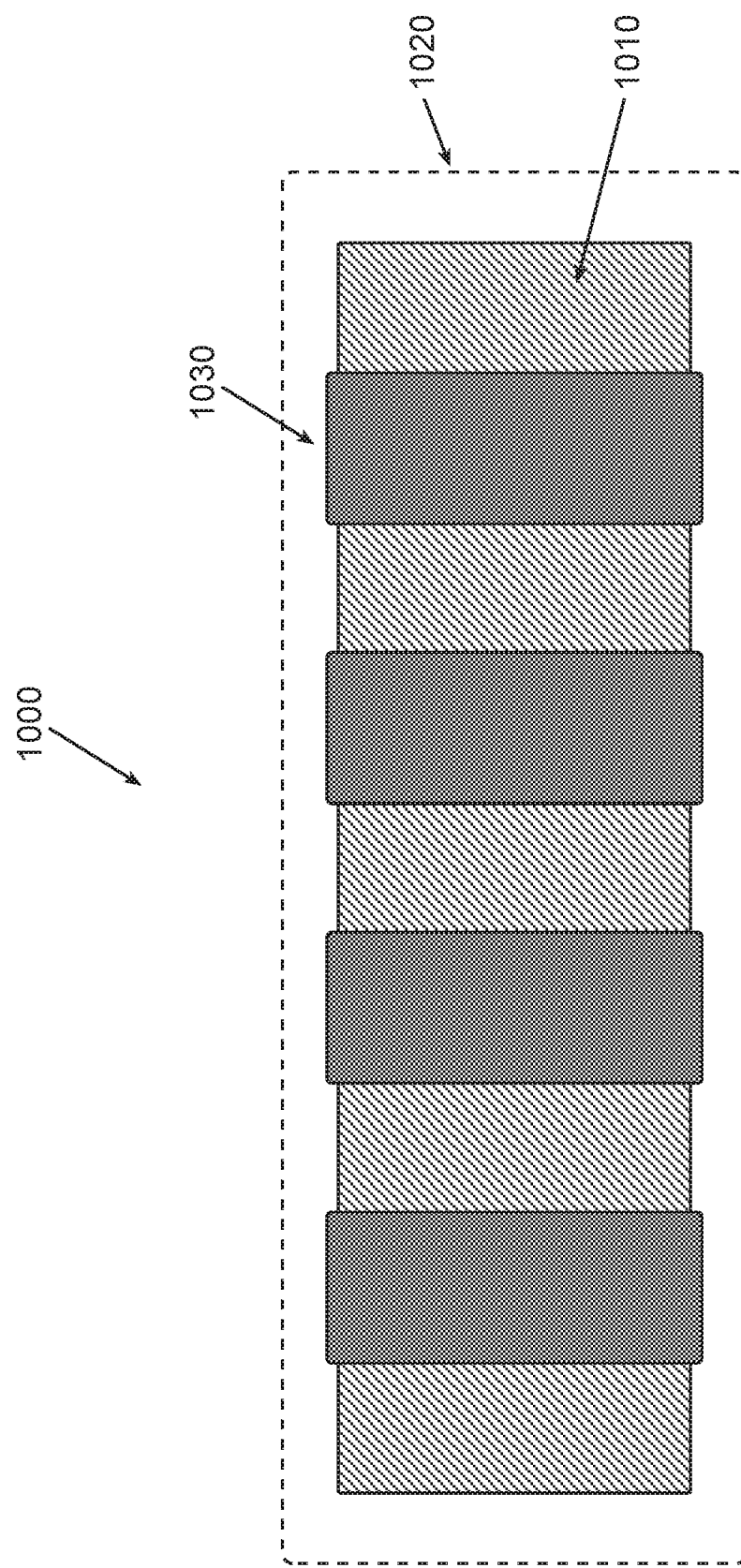
FIG. 10 is shows the poly-elastic strap, casing and vertical seams according to an embodiment of the invention.

Also shown in FIG. 1 is 110, which is a variable tension poly elastic strap. In certain embodiments, the strap has a thickness of 4 inches. Also shown are 115 which are the vertical seam lines. In certain embodiments, there are two vertical seam lines for garment devices for women and 4 seam lines for garment devices for men (see FIG. 10 showing the seams as vertical lines). Element 130 is the poly-tensile sheath casing which in certain embodiments envelopes the strap.

Figure 2:
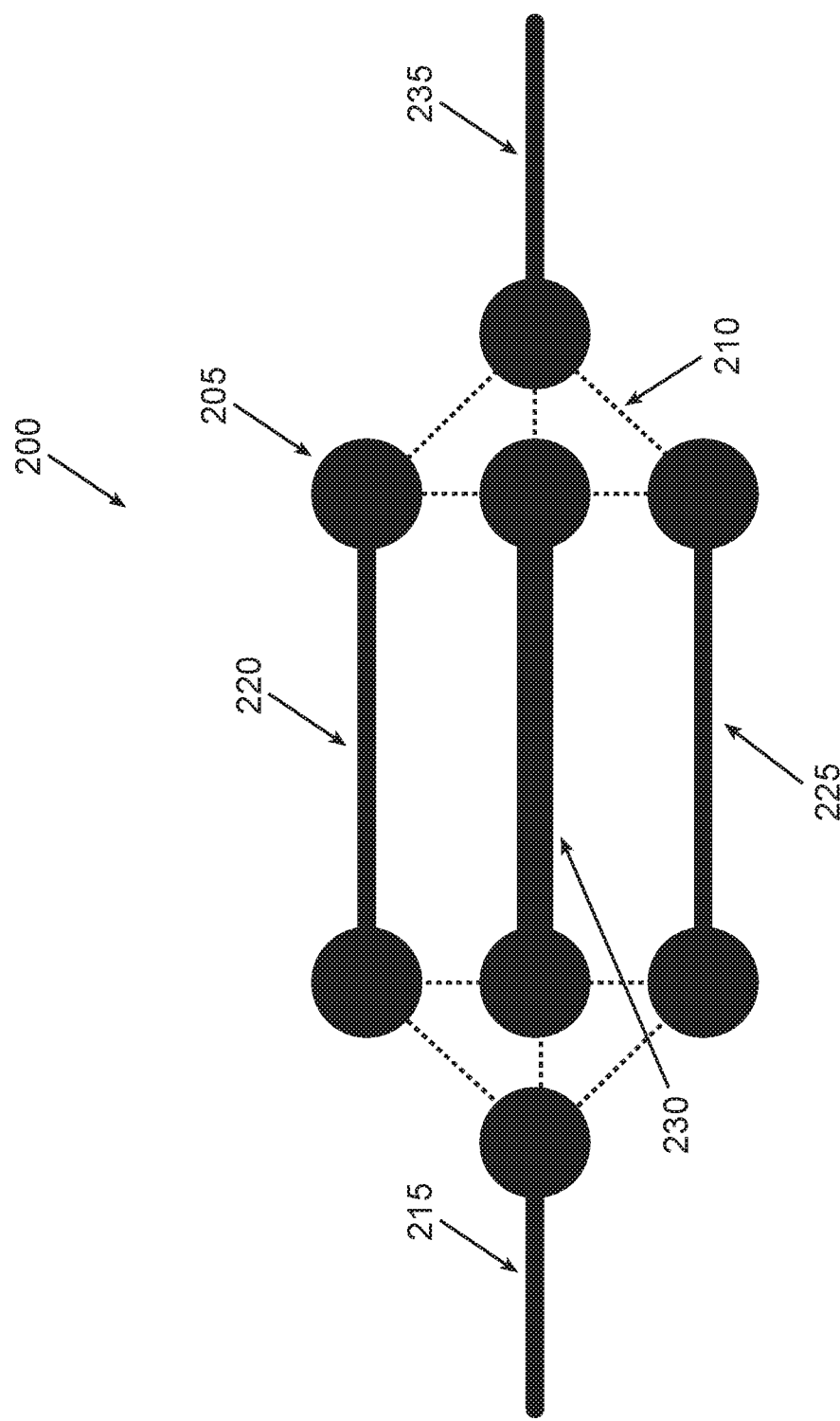
FIG. 2 is a schematic view of the elastic strap from the garment of FIG. 1.

Referring now to FIG. 2, the strap casing and device integration 200 is shown. A connection point (black circle) 205, stitching, either blind or welded (dotted lines) 210, superior mesh 215, exterior casing 220, interior casing 225, elastic strap 230, inferior mesh 235 is shown.

Figure 3:
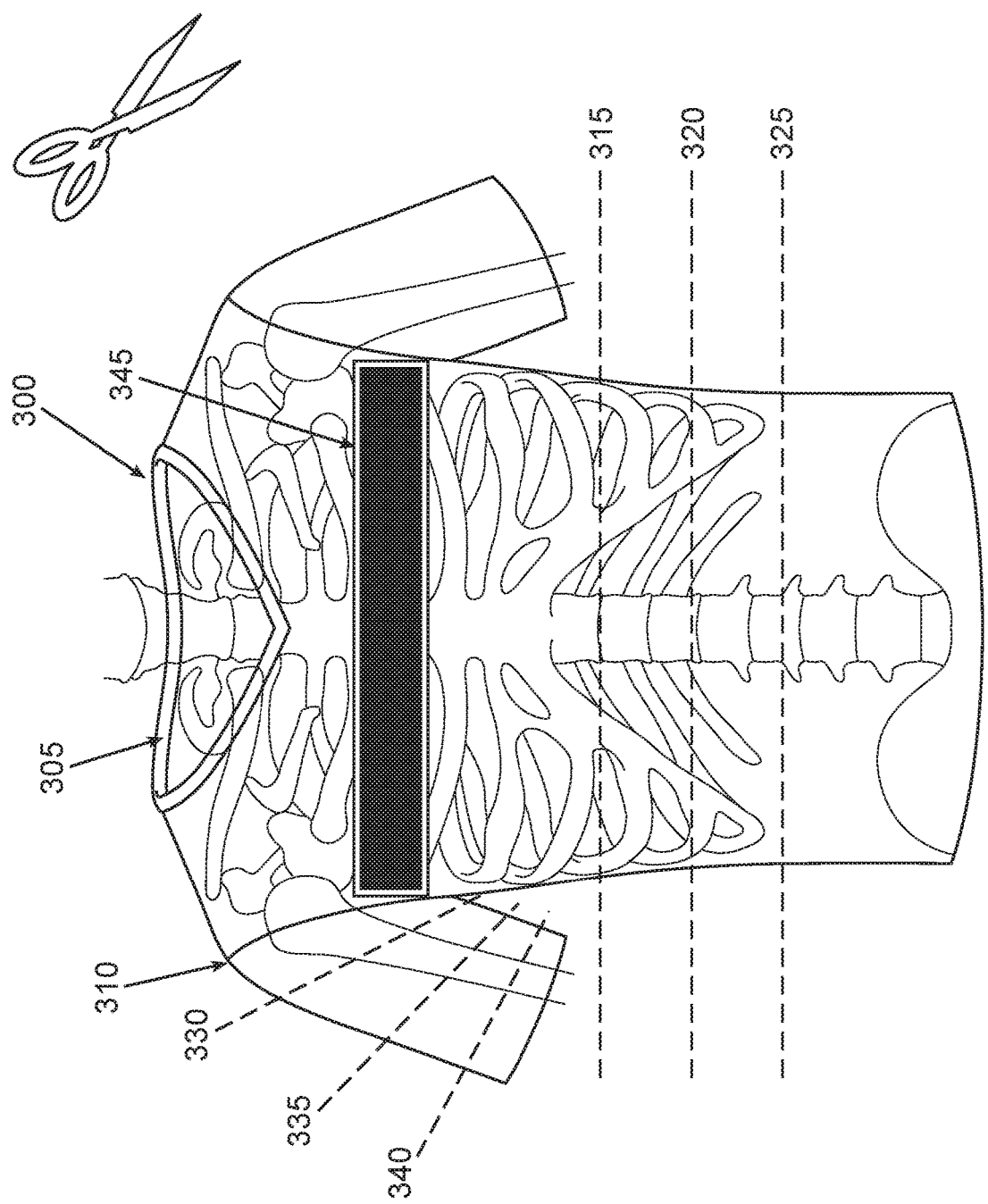
FIG. 3 is an anterior view of the garment device superimposed over a human skeletal model for biomedically tailored reference points.

Referring now to FIG. 3, this is a posterior view of the garment device. As it's connected to the front, the device is made out of the same strong power mesh with the same sleeve length as the anterior of the garment. It has the same attachment point as the front of the garment, and just as the front, it's constructed with a shortened length—in this current embodiment stopping just below the T-8 vertebrae. There is a four-inch-wide poly elastic strap that is horizontally sewn into the garment, attached to the arm seam fabric such that the medial points of each scapula are connected. This poly elastic strap is further segmented by four, evenly spaced vertical seam lines that regulate and disperse the tension of the strap, thus preventing the application of excessive force to the wearer when the shoulders are in neutral position. This poly elastic strap is sheathed by a casing that provides comfort to the wearer. In certain embodiments, the casing is made of the same fabric as a secondary garment to which the garment device is attached to.

Furthermore, the strap length is graded (sized) specifically to each garment size that the device is being sewn into, providing a custom-built solution to each piece of fabric and giving the wearer a comfortable way for proprioception with regulated shoulder retraction. The poly elastic strap assists the wearer in a natural, scapula retraction that uses the body to achieve correct postural alignment through mirroring and augmenting the muscles that are primarily associated with such contraction.

Referring now to FIG. 3, a full-length mesh body garment is shown superimposed onto a human skeletal model for biomedically tailored reference points 300. The primary attachment point, or integration intersection, is chosen along the posterior rim of the collar, because this point of contact between the two garments is the most stable and least likely to experience shifting. The anatomical position of the attachment point is the nape of the neck, otherwise referred to as the "nuchal" point in medical terminology. The device can be sewn in via nuchal attachment point 305 or axilla attachment point 310 to any traditional garment and essentially be unnoticeable to the casual observer. As shown in the embodiment of FIG. 1, the device has a shortened, chest length construction so that it can easily be sewn into any upper garment. More specifically, the garment device terminates just below the pectoralis major However, in this embodiment it is shown with a longer length and three possible alternate termination points, 315, 320, 325. Similar to the shirt length, the sleeve length 330, 335, 340 can also be adjusted to the wearer's preference or the intended overlaying garment. While the elastic strap 340 is depicted in primarily the dimensions shown in the drawings as 4 inches wide, this width may vary in addition to the elastic material, in order to change the degree of tensile strength and resulting force applied to the wearer. The length of the elastic strap, however, should remain relatively constant, being altered only to accommodate variable sizes in the wearer. It is contemplated that variations will range from petite to large, although a custom elastic strap length can easily be fabricated.

It is contemplated that the garment, by retracting the scapula, will assist in weight lifting training regimens and competition, by improving the wearer's form throughout the lift. A retracted scapula creates a more stable base and results in the recruitment of relatively more chest muscle groups, as opposed to the weaker shoulder muscle groups. Due to the user recruiting a stronger muscle as the primary mover for an exercise, there will be faster progress in training and improved performance for competitions.

Figure 4:
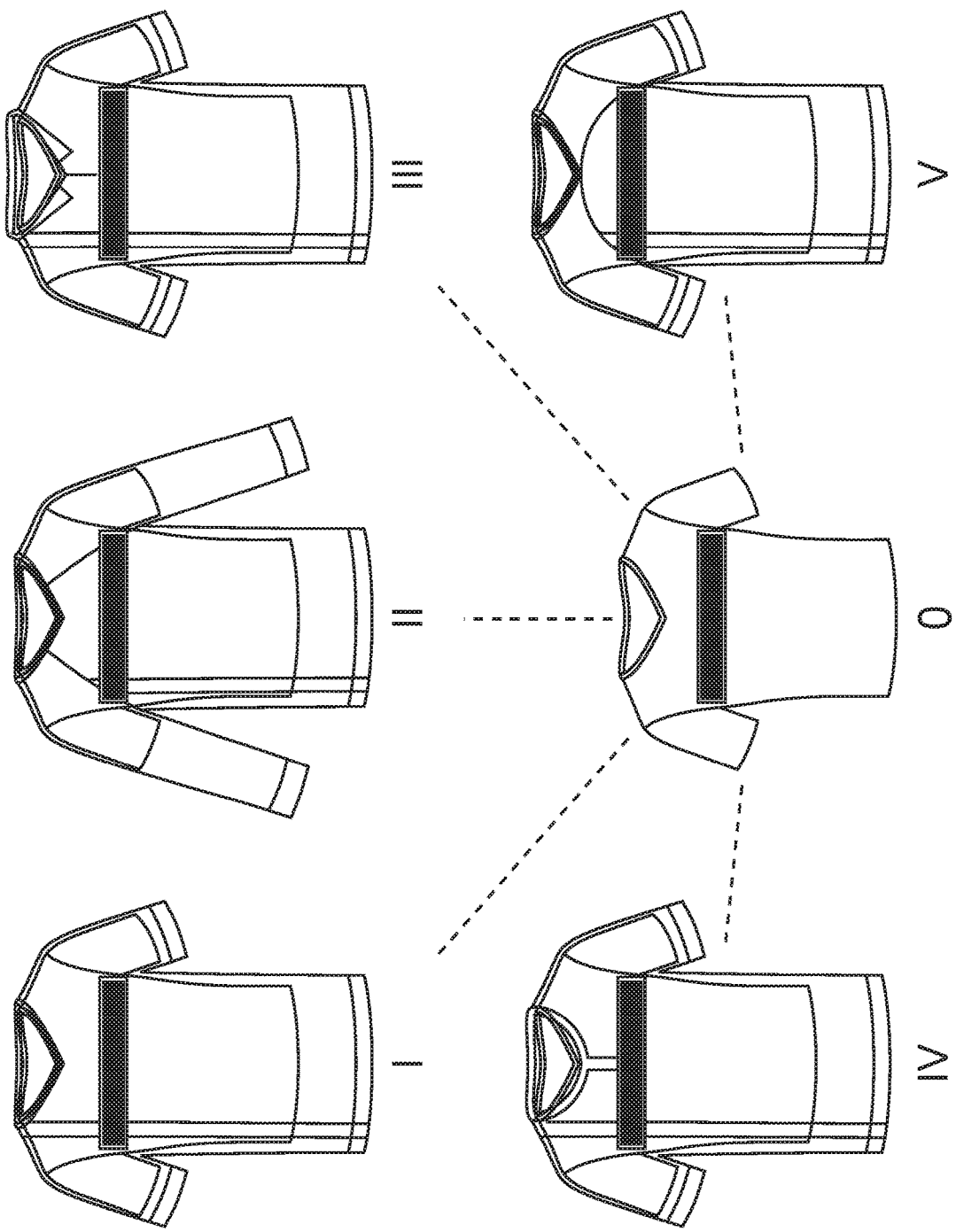
FIG. 4 is an anterior and translucent view of the garment device as sewn into multiple types of garments.

Referring to FIG. 4 are various types of garment (secondary garment) which the garment device is configured to be sewn into or manufactured into in a pre-assembled state.

Dynamic Proprioceptive Muscle Correction

Figure 5B:
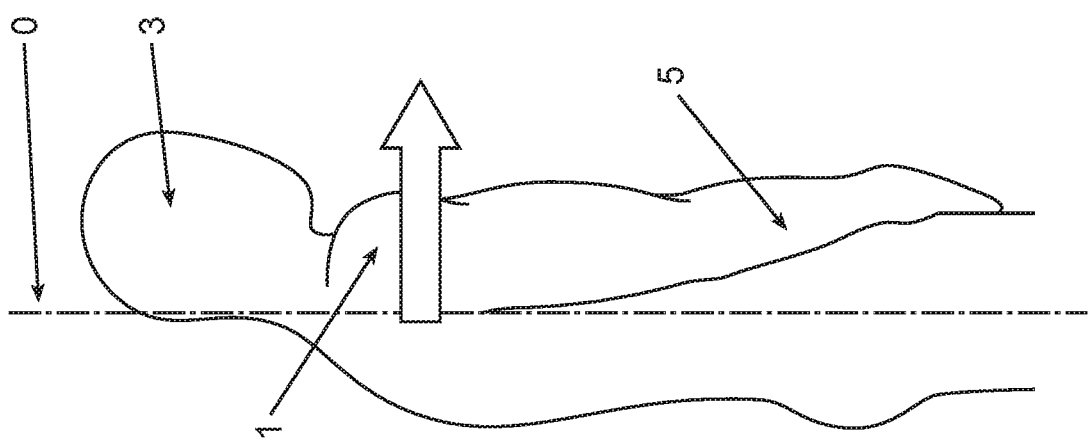
FIG. 5A-5B is a two part diagram of rounded shoulders aka protracted shoulder girdle compared to good posture with relatively retracted scapulae.
Figure 5A:
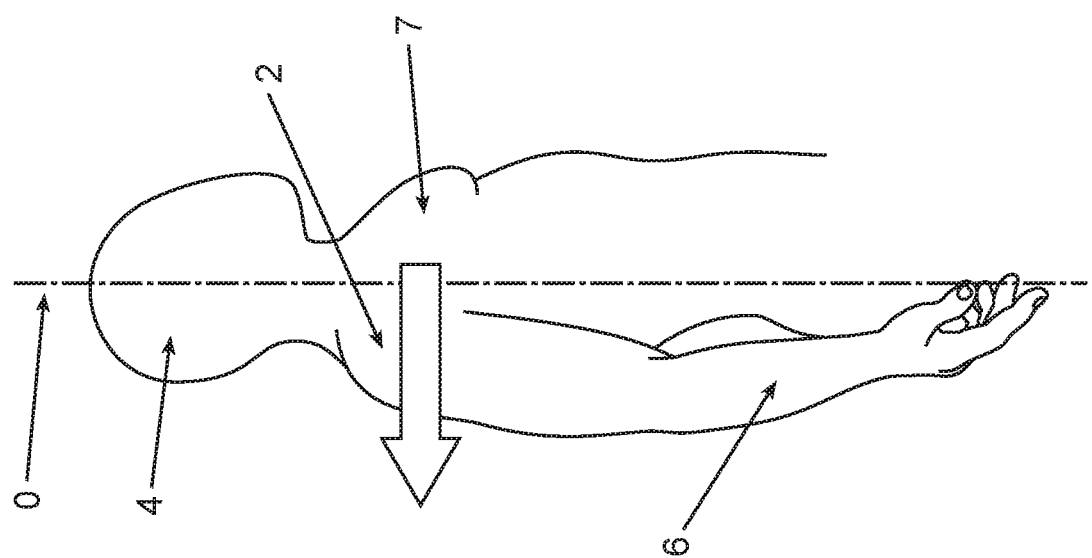

Referring to FIG. 5, a diagram of Rounded shoulders aka protracted shoulder girdle VS. Good Posture is shown. Elements shown are Midline 0, Protracted shoulders 1, Retracted shoulders 2, Compensatory head posture (stooping or tilting), chronic forward head posture, postural distortion, anterior head carriage 3, Correct head posture 4, Arms in front of midline 5, Arm behind the midline 6, Chest is more open and breathing enhanced 7.

Figure 6A:
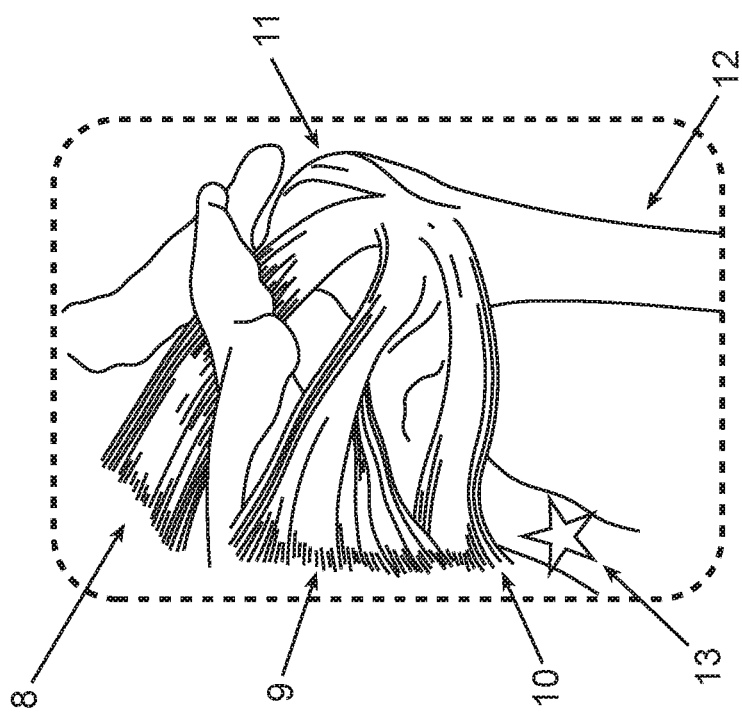
FIG. 6A-6B are posterior anatomical views of the back and shoulder musculoskeletal architectures.
Figure 6B:
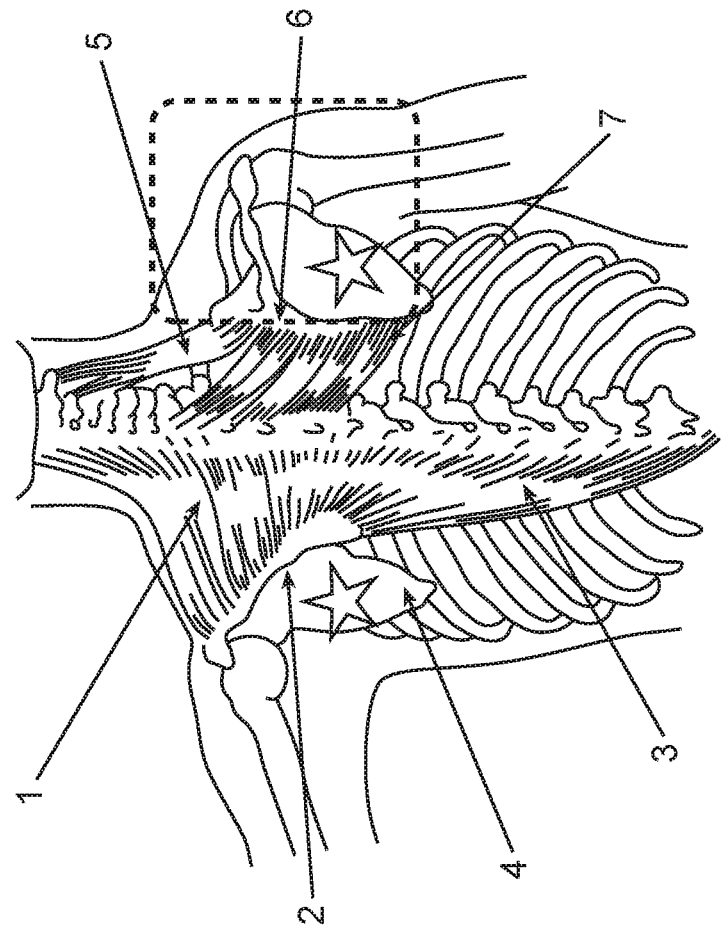

FIG. 6A depicts the trapezius and rhomboid musculature and surrounding skeletal anatomy. FIG. 6B depicts the shoulder, also known as the glenohumoral joint, is the most flexible and mobile junction in the human body having up to 180 degrees of flexion; and as such is prone to several common malfunctions. The shallow glenoid cavity, while allowing maximum range of movement, is also extremely vulnerable to insults, thus the surrounding glenohumoral ligaments and muscles must be strengthened to a degree that will prevent dislocation.

FIG. 7A-7B depicts the mechanism of action and the dynamic effect 700 it has on a wearer's posture. The garment device consists of two primary types of fabrics that mimic the motion and contraction of the rhomboids and upper trapezius.

The vertically segmented elastic strap, is mounted in the center, posterior of the garment device. The vertically segmented elastic strap, precisely overlays the rhomboids and upper trapezius. When the shirt is donned by the user, the elastic strap 705 is slightly stretched (or extended). Due to the stretch of the elastic, pull 720 is created toward the spine, mirroring the contraction of the rhomboids and upper trapezius. If the user holds perfect posture with his/her own musculature the vertically segmented elastic strap 710 applies very little pressure. As the user allows his/her shoulders to "roll" forward, the vertically segmented elastic strap applies greater tension 715.

The PPR Mesh (or similar fabric) 725 encapsulates the upper arm, shoulder and upper back. This allows the Vertically segmented elastic strap to attach to the medial point of the scapula. The tension and force of the strap is distributed across the entire front and rear shoulder area diffusing uncomfortable pressure points and providing retraction by "pulling" from the front and rear of the shoulder simultaneously.

This method of retraction differs from other products. Competitors use vertical straps sewn into a garment that run from the upper shoulder or chest, down the back and terminating at the buttox. The force of these straps are applied to the upper insertion points of the straps (which they call NeuroBands). The problem with these types of shirts is that the entire body has to be tight and if the wearer does not exactly fit the garment it is ineffective. The PPR's benefit is that it applies diffused horizontal tension that mirrors the anatomy and the body of the garment can be loose or tight depending upon the user's preference.

The complete arc of movement that the shoulder joint is capable of resembles that of a "seesaw" motion. Medical terminology refers to this as the scapulohumeral rhythm and it can be thought of in two complimentary and overlapping steps. Initially the humerous is retracted in the posterior direction for the first 25-50% of the flexion, then the scapula.

Figure 8:
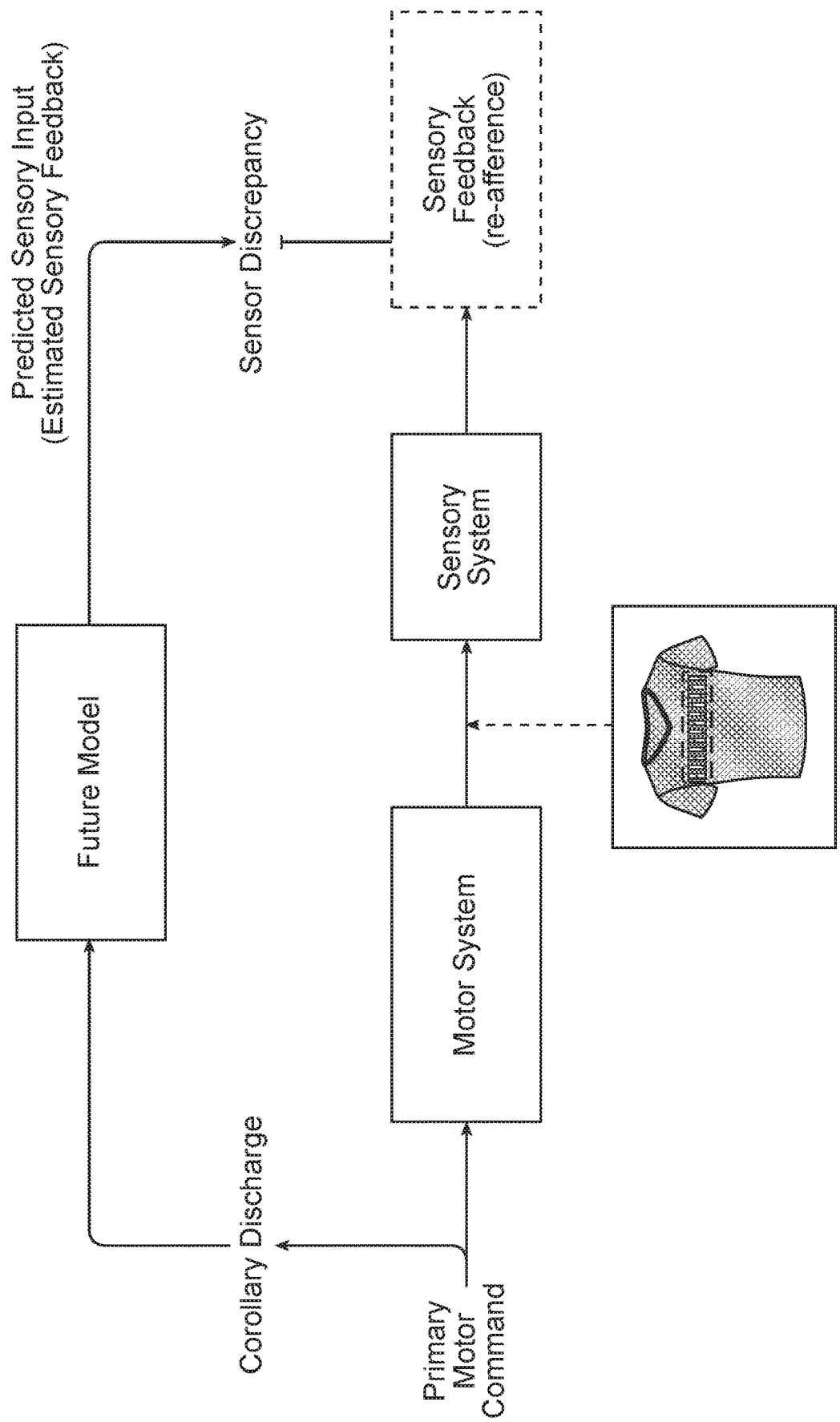
FIG. 8 is a flow diagram of the signal processes involved in proprioception and the targeted effect of the garment device.

FIG. 8 is a flow diagram of the signal processes involved in proprioception and the targeted effect of the garment device.

Figure 9:
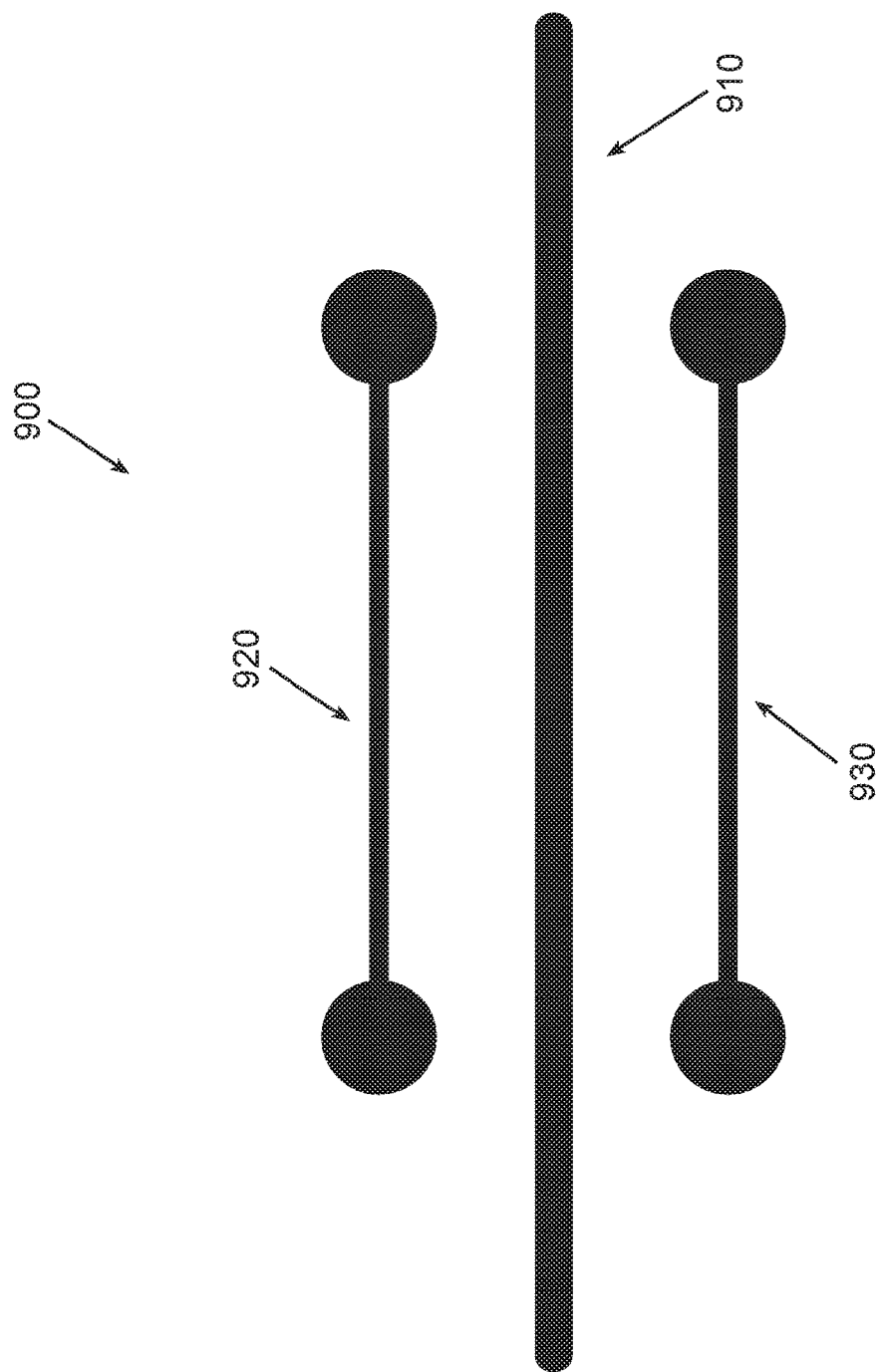
FIG. 9 is an embodiment of the casing material shown with the elastic strap and enveloping the elastic strap.

FIG. 9 is an embodiment of the casing material 920, 930 shown with the elastic strap 910 and enveloping the elastic strap 910.

FIG. 10 is shows the poly-elastic strap 1010, casing 1020 and vertical seams 1030 according to an embodiment of the invention. FIG. 10 shows the vertical seams 1030 being evenly spaced throughout.

Having thus described several embodiments for practicing the inventive method, its advantages and objectives can be easily understood. Variations from the description above may and can be made by one skilled in the art without departing from the scope of the invention.

Accordingly, this invention is not to be limited by the embodiments as described, which are given by way of example only and not by way of limitation.

What is claimed is:

1. A method for manufacturing a garment device for correcting a wearer's posture, comprising:
   providing a mesh body;
   inserting a variable tension poly-elastic strap with at least one vertical seam into an elastic strap casing that is stitched onto the mesh body,
   wherein the variable tension poly-elastic strap is configured to correct the wearer's posture to a natural posture by pulling portions of the musculo-skeletal frame into correct postural alignment.

2. The method of claim 1, wherein the elastic strap is configured around the medial point of the scapula of the wearer.

3. The method of claim 1, wherein a casing is integrated into the construction of the elastic strap to provide comfort to the wearer.

4. The method of claim 1, wherein the mesh body is breathable.

5. The method of claim 1, wherein the variable tension poly-elastic strap includes at least two seams and wherein the at least two seams are evenly spaced along the variable tension poly-elastic strap.

6. The method of claim 1, wherein the mesh body is made from materials chosen from the group consisting of: nylon, spandex, cotton, polyester, chiffon, denim, lace, leather, wool, or a combination thereof.

7. The method of claim 1, wherein the variable tension poly-elastic strap ceases posterior pull and allows for a full range of motion for the wearer and the restriction of movement is minimized.

8. The method of claim 1, wherein the mesh body has a variable length selected from a group consisting of: a shortened length stopping just below the chest, an extended length stopping below the waist, and a medium length stopping at the bellybutton/midsection length.

9. The method of claim 1, wherein the variable tension poly-elastic strap provides postural support to a wearer suffering from less than ideal posture, or suffering a related malady selected from the following group consisting of: rounded shoulders, scapular dysknesis, kyphosis, forward head, lordosis, scoliosis, rounded shoulder from cervical spine injury, rotator cuff tears, shoulder pathologies, acromioclavicular joint separation, arthritis, and general posterior musculature weakness.

10. The method of claim 1, wherein the variable tension poly-elastic strap ceases posterior pull and allows for a full range of motion for the wearer and the restriction of movement is minimized.

11. The method of claim 1, wherein the mesh body includes sleeves, and wherein the sleeves of the mesh body extend at least below the deltoid of the wearer.

12. The method of claim 11, wherein the sleeves of the mesh body extend to fit a long sleeve or short sleeve shirt.

* * * * *